United States Patent [19]

Tolbert et al.

[11] 4,335,215
[45] Jun. 15, 1982

[54] METHOD OF GROWING ANCHORAGE-DEPENDENT CELLS

[75] Inventors: William R. Tolbert, Manchester; Mary M. Hitt, St. Louis; Joseph Feder, University City; Richard C. Kimes, Creve Coeur, all of Mo.

[73] Assignee: Monsanto Company, St. Louis, Mo.

[21] Appl. No.: 181,582

[22] Filed: Aug. 27, 1980

[51] Int. Cl.³ .................... C12N 5/02; C12M 3/02; C12M 1/24; C12P 1/00
[52] U.S. Cl. .................... 435/241; 435/286; 435/296; 435/41; 435/68; 435/811
[58] Field of Search .......... 435/241, 286, 240, 284, 435/813, 811, 41, 296, 316, 287, 256, 285

[56] References Cited

U.S. PATENT DOCUMENTS

| | | | |
|---|---|---|---|
| 2,967,107 | 1/1961 | Geiger et al. | 426/16 |
| 3,234,026 | 2/1966 | Coutts et al. | 435/813 |
| 3,591,460 | 7/1971 | Smith | 435/286 |
| 3,647,633 | 3/1972 | Dawson | 435/286 |
| 3,717,551 | 2/1973 | Bizzini et al. | 435/241 |
| 3,880,716 | 4/1975 | Engelbart et al. | 435/313 |
| 4,036,693 | 7/1977 | Levine et al. | 435/240 |
| 4,189,535 | 2/1980 | Levine et al. | 435/68 |

FOREIGN PATENT DOCUMENTS

901673 7/1962 United Kingdom ............... 435/240

OTHER PUBLICATIONS van Hemert et al., Homogeneous Cultivation of Animal Cells for the Production of Virus and Virus Products, *Biotech. Bioeng.*, vol. XI, 1969, 875–885.
Bulletin 1068, "Bio-Carriers TM for Cell Culture", Bio-Rad Labs, 1979, 4 pages.
Bulletin "Cytodex TM 1–Beaded Microcarriers for Cell Culture", pp. 5 & 18, Pharmacia Fina Chemicals, May 1, 1978.
Bulletin "Superbead TM Microcarriers–Instructions for Use", Flow Laboratories, Inc., Nov. 1978, 2 pages.
Jakoby et al., *Methods in Enzymology*, vol. LVIII, Cell Culture, 1979, pp. 204, 209, 210.

*Primary Examiner*—Alvin E. Tanenholtz
*Assistant Examiner*—Kathleen S. McCowin
*Attorney, Agent, or Firm*—Scott J. Meyer; James W. Williams, Jr.

[57] ABSTRACT

Anchorage-dependent cells are grown in agitated microcarrier suspension in which the cells and microcarriers are aggregated by periodically providing a temporary residence of said microcarriers and cells outside the main cell culture reactor agitation zone and in a separate compartment wherein they are subjected to a gentle tumbling action within a confined space having substantially the same environmental conditions as in the main cell culture reactor.

10 Claims, 3 Drawing Figures

METHOD OF GROWING ANCHORAGE-DEPENDENT CELLS

BACKGROUND OF THE INVENTION

This invention relates to a method for the culture of cells and, more particularly, to the submerged culture of animal cells using microcarriers for the attachment of cells in suspension.

In recent years there has been rapid growth in the development of various methods for the culturing of cells in suspension. The attainment of high cell densities is a primary objective of many of these approaches. The use of a cell culture vessel with controlled agitation by means of a magnetic stirrer bar or a mechanically driven impeller on a shaft is a typical feature of these methods. Examples of such apparatus are disclosed in U.S. Pat. Nos. 2,958,517; 3,639,932; 3,572,651, 3,622,122; and 3,649,465. These are essentially batch type spin culture devices or spinner flasks in which the cells are incubated in a fixed amount of nutrient under appropriate culture conditions until cell growth has ceased.

Continous cell culture systems and apparatus also have been described heretofore in which fresh culture medium can be added and spent medium can be separated from the growing cells by filtration and withdrawn from the flask on a continuous or semi-continuous basis as seen from U.S. Pat. Nos. 4,166,768 and 4,178,209.

While ordinary suspension cultures are suitable for growth of certain mammalian cell lines, other cells, and particularly human diploid cells, are anchorage-dependent in that they require support surface means for cell attachment. Examples of such cell culture systems are the monolayer growth systems in T-flasks, roller bottles, artificial capillary propagators and multi-plate propagators.

In order to provide the advantages of large scale suspension culture with provision for cell attachment, microcarrier systems have been developed. The successful use of microcarriers for cell culture was first reported by van Wezel, *Nature* 216, 64–65 (1967). The method of van Wezel consisted of growing cells as monolayers on the surface of positively charged DEAE-Sephadex® beads (grade A-50, about 100μ diameter) suspended in culture media in a stirred vessel. The stirred vessel used by van Wezel was the Bilthoven microbial culture unit described by van Hemert, *Biotechnol. Bioeng.* VI, 381–401 (1964). In this method, different cell lines, human diploid cells, and primary rabbit kidney cells were successfully cultivated. The production of polio virus in the microcarrier culture was examined by van Wezel and the virus multiplication was found to be essentially similar to that in monolayer culture. Further description of that microcarrier system is disclosed by van Wezel et al., *Process Biochem.*, March 1978, pp. 6–8 and 28, wherein it is stated that as far as cultivation of very sensitive cell types, such as human diploid cell strains is concerned, the system is still not completely satisfactory.

A modification of the van Wezel method is described by Levine et al, *Somatic Cell Genetics* 3, 149–155 (1977) and U.S. Pat. Nos. 4,036,693 and 4,189,534. This system uses essentially a spinner flask with a magnetically driven stirrer bar. Some success with this system at a small scale of 100 ml working volume has been reported by Levine et al., *Biotechnol. Bioeng.* 21, 821–45 (1979). However, other investigators have cast doubt upon the applicability of this system to larger scale use with human diploid cells; Lewis and Volkers, *Develop. Biol. Standard.* 42, 147–151 (1979).

In copending application Ser. No. 161,614, filed June 20, 1980, and now U.S. Pat. No. 428,854 and assigned to a common assignee, an improved cell culture system and apparatus is disclosed which is particularly useful for adaptation to cell culture on microcarriers in agitated suspension media. The agitator has flexible sheets which provide a gentle agitation for sensitive cells and fragile microcarriers.

BRIEF DESCRIPTION OF THE INVENTION

In accordance with the present invention, an improved cell culture method is provided for the agitated suspension culturing of cells on microcarriers. The method involves the formation of aggregates of microcarriers whereby the cells grow not only on the surface of the microcarrier beads but also between the beads with many cells extending between adjacent carriers thereby forming a cocoon of cells surrounding the aggregated carriers. This aggregation greatly increases the number of cells that are produced per unit area of carrier surface. The desired aggregation is carried out by periodically providing the microcarrier beads and attached cells with a temporary residence outside the normal agitation zone of the primary or main cell culture reactor and in a separate zone or compartment wherein they are subjected to a gentle tumbling action within a confined space having substantially the same environmental conditions as in the primary cell culture reactor.

Following each such periodic residence outside the main cell culture reactor agitation zone, the microcarriers are recycled to said reactor and the entire process is carried out on a continuous or semi-continuous basis until the desired cell density for cell harvest is attained.

DETAILED DESCRIPTION OF THE INVENTION

While the specification concludes with claims particularly pointing out and distinctly claiming the subject matter regarded as forming the present invention, it is believed that the invention will be better understood from the following description in connection with the accompanying drawings in which:

Figure 1:
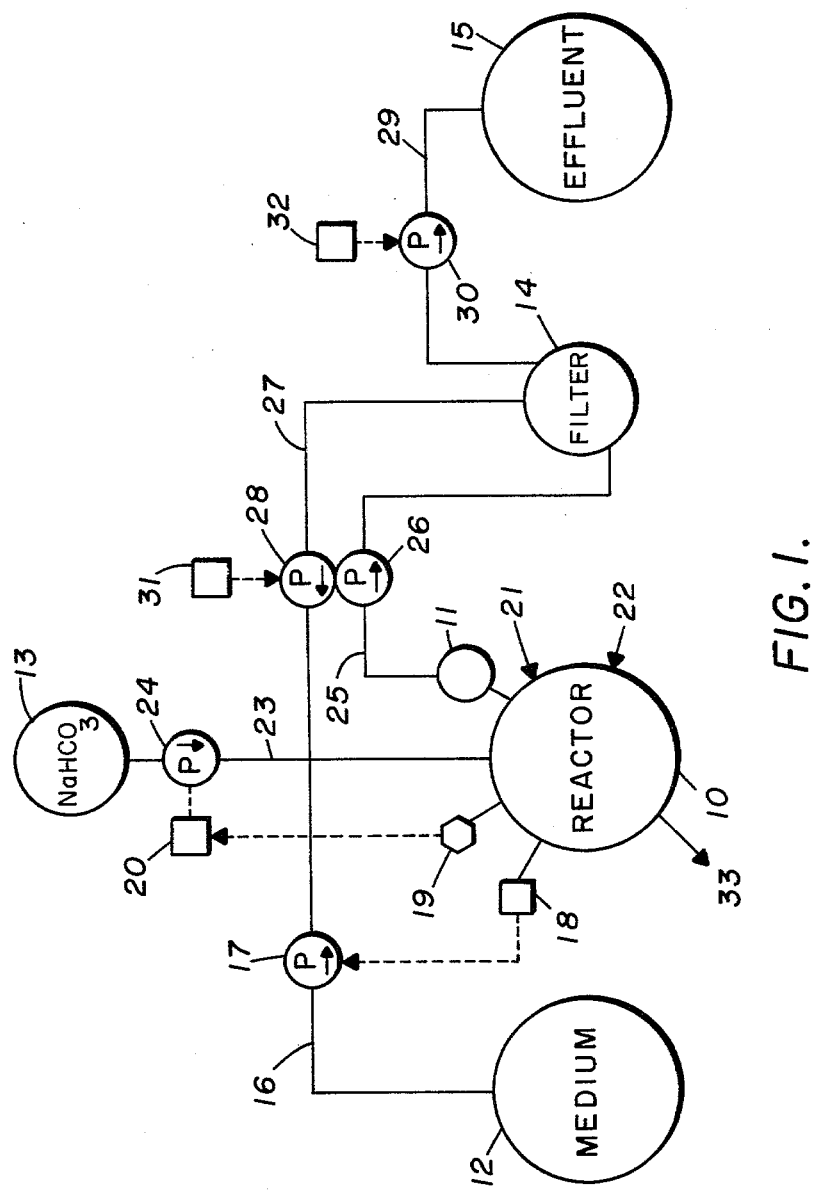
FIG. 1 is a schematic diagram showing a cell culture system and apparatus in accordance with a preferred embodiment of the invention.

Referring now to FIG. 1 of the drawing, a series of interconnected cell culture vessels is shown comprising a main cell culture reactor or growth vessel 10, a fresh medium reservoir 12, a NaHCO$_3$ reservoir 13, a satellite filter vessel 14 and an effluent reservoir 15. Cells are grown attached to microcarriers in agitated liquid suspension of nutrient medium in the cell culture reactor 10. Additional fresh medium is pumped through line 16 into the cell culture reactor as needed from reservoir 12 by a peristaltic pump 17. A constant liquid level (e.g., 4 liters or 44 liters, depending on the capacity of the reactor) is maintained in reactor 10 by a capacitance level control system 18 attached to the outside of the cell culture reactor and in actuation relation with pump 17. Continuous pH control is provided by an autoclavable pH monitoring electrode 19 submerged in the cell culture reactor 10 through a rubber stopper in a vessel side arm which is connected to a pH controller 20.

A $CO_2$ in air mixture 21 is passed over the cell culture suspension surface in reactor 10 and oxygen 22 is sparged when necessary. Above pH of about 7.1, a high $CO_2$-air mixture (10–15% $CO_2$) flows over the surface of the liquid in the cell culture reactor whereas below pH of about 7.1, a low $CO_2$-air mixture (2–5% $CO_2$) is used. Below pH of about 7.0, an aqueous solution of 0.5 M $NaHCO_3$ is pumped through line 23 into the cell culture reactor from reservoir 13 by a peristaltic pump 24 activated by pH controller 20 as needed to maintain a pH > 7.0. A low oxygen sparge (about 0–2 ml/minute) is used to maintain a dissolved oxygen level within a range of from about 10 to about 140 mm Hg partial pressure and preferably within a range of from about 30 to about 80 mm Hg partial pressure.

The suspension with cells and microcarriers is periodically removed in part from the main cell culture reactor through a settling chamber 11 where the relatively dense cells and microcarriers are allowed to settle and aggregate during a temporary residence period while the less dense culture medium is pumped through line 25 into satellite filter vessel 14 by peristaltic pump 26. The culture medium thus flows by pressure differential from below the liquid level in the cell culture reactor through the settling chamber and thence to near the bottom of the satellite filter vessel. Unfiltered medium is periodically pumped through line 27 back into the top of cell culture reactor 10 from near the top of the satellite filter vessel by peristaltic pump 28. Filtered expended medium is periodically pumped through line 29 into effluent reservoir 15 from the satellite filter vessel by peristaltic pump 30. Pulse timer 31, which is connected to pumps 26 and 28, or preferably to a double headed pump, regulates the periodicity of circulation of medium between the main cell culture reactor and the satellite filter vessel while pulse timer 32, which is connected to pump 30, regulates the flow of expended medium from the satellite filter vessel to the effluent reservoir. Sampling and harvest of cells from the cell culture reactor at 33 can be had as desired.

The net flow rate in the recycling system preferably does not exceed about one-tenth the settling bottle volume per minute and preferably is greater than about 1.1 times the effluent flow rate. The effluent flow rate (equal to the flow of fresh medium into the system) is determined by the metabolic requirements of the particular cells growing in the main cell culture reactor. For example, in the case of human diploid foreskin fibroblasts, the optimum fresh medium (or effluent) flow rate is from about 4 to about 8 ml/hour per $10^9$ cells in the reactor. In illustrative settling bottles having volumes of about 150 ml for the 4 liter reactor and about 1000 ml for the 44 liter reactor, the maximum cell concentrations will range up to about $2 \times 10^7$ and to about $4 \times 10^7$ cells/ml, respectively. The recycle pumps can preferably be reversed for periods of up to about one-fourth the total forward time in order to maintain free movement of microcarrier beads in the narrower portions of the settling bottle. These pumps can also be turned off periodically for up to 30 seconds per minute to enhance settling.

The formation of aggregates of microcarriers is critical to the method of the invention. This can be carried out by providing the microcarrier beads and attached cells with a temporary residence outside the normal agitation zone of the main cell culture reactor 10 and in a separate zone or compartment such as in the settling chamber 11 where they are subjected to a gentle tumbling action in a confined space having substantially the same environmental conditions as in the main cell culture reactor. The settling chamber 11 is conveniently located in or attached to the main cell culture reactor. It is important in enhancing aggregate formation to provide for close contact between microcarriers and cells during the settling process over an extended period of time. These contacts can take place in a non-static environment with medium perfusing around the beads into the recycling system of the satallite filter vessel 14.

Residence time of the microcarrier beads and cells in the settling chamber preferably ranges from about one to about ten minutes from the time they are periodically drawn into the settling chamber until the time they fall back into the main cell culture reactor zone.

The main cell culture reactor preferably is of the type disclosed in copending application Ser. No. 161,614, filed June 20, 1980, assigned to a common assignee, the disclosure of which is incorporated herein by reference. Said cell culture reactor comprises a flask assembly in which the culture medium is gently agitated by the slow rotation of one or more relatively large surface area, flexible sheets of an agitator means suspended downwardly in the culture medum. The flexible sheets have a total surface area on one side which preferably ranges from about 0.25 to about 1.0 times the available traversable cross-sectional area of the culture fluid-containing portion of the culture vessel. These flexible sheets are positioned on the agitator in a manner to allow them to billow out like sails as liquid spills from their trailing edges during rotation of the agitator means, preferably within a range of from about 5 to about 100 rpm.

Figure 2:
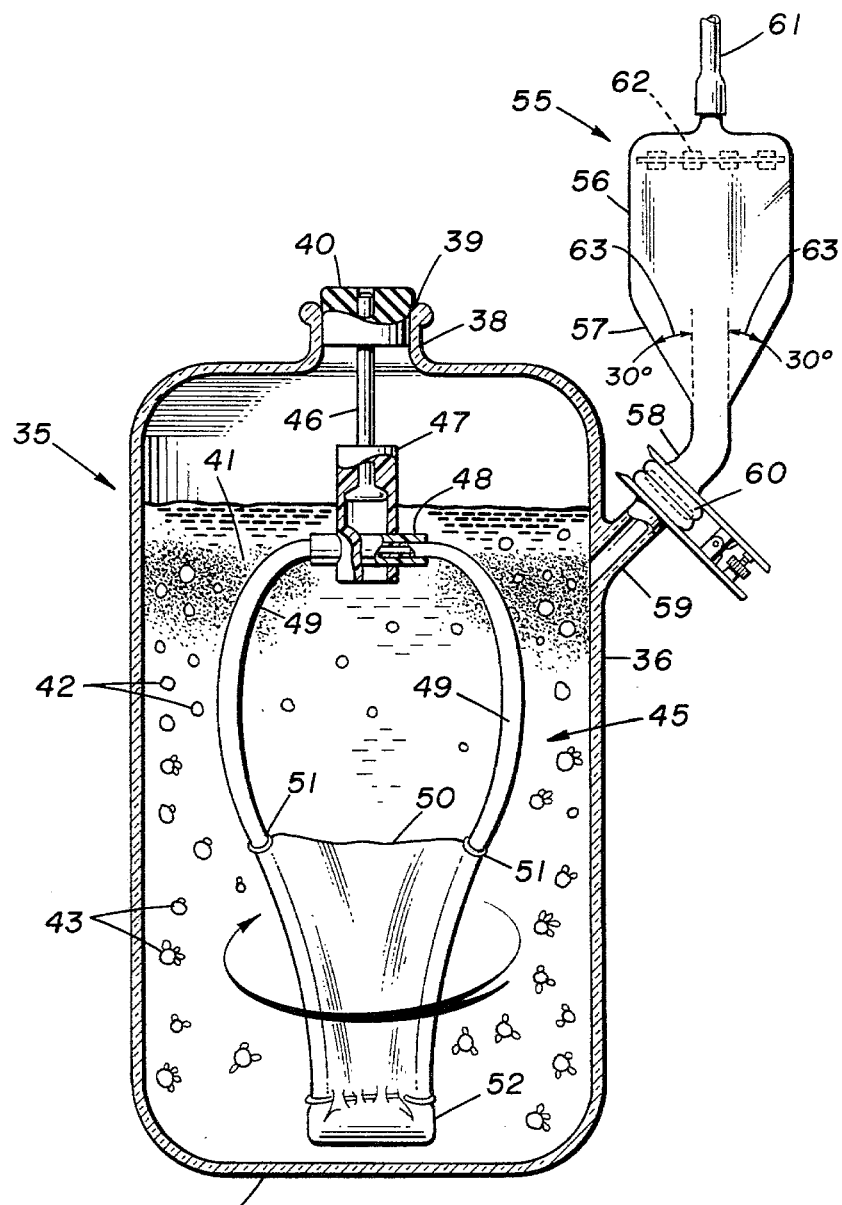
FIG. 2 is a side elevation view partly in cross section showing a cell culture vessel and settling chamber employed in the method of the invention.
Figure 3:
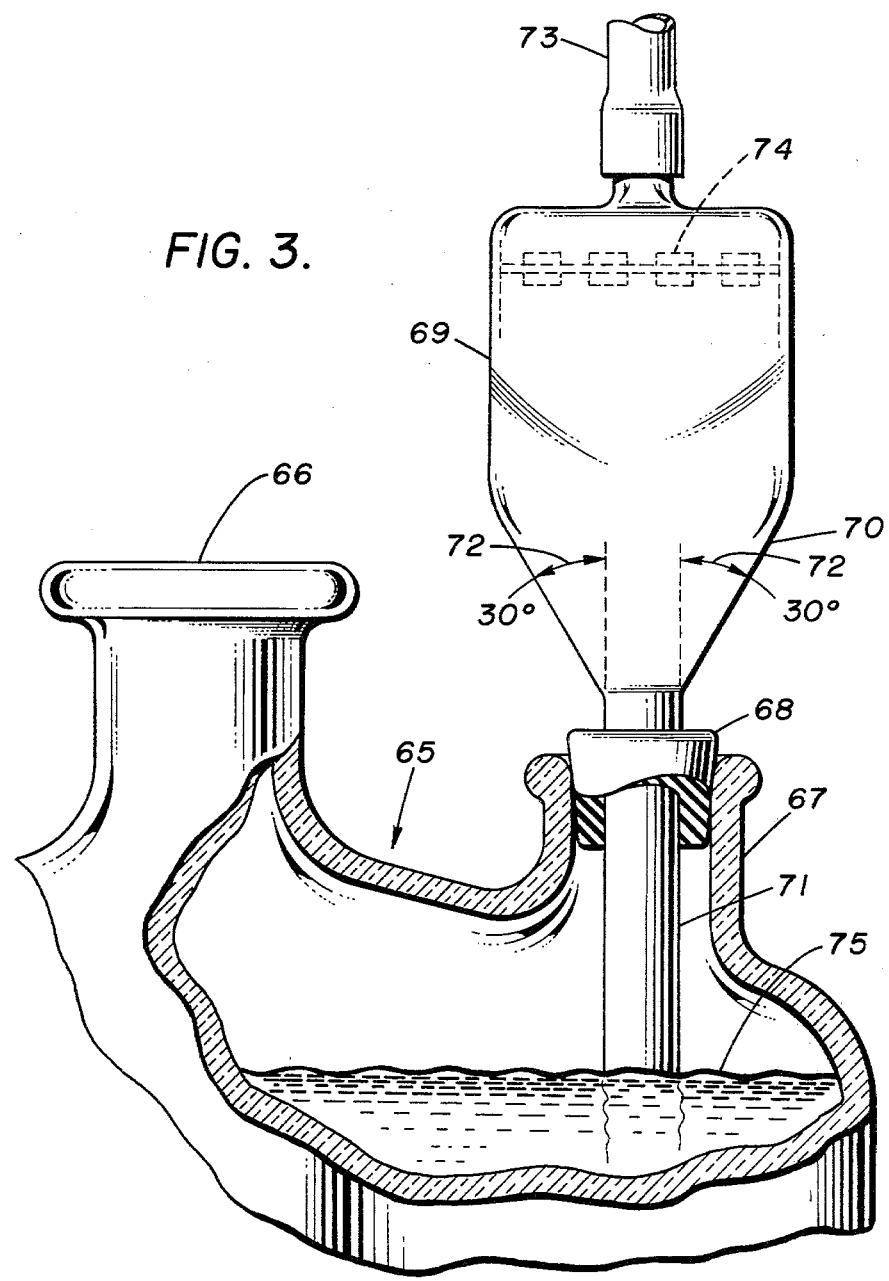
FIG. 3 is a side elevation view partly in cross section showing another embodiment of a cell culture vessel in part and an attached settling chamber employed in the method of the invention.

The settling chamber employed in the present invention can be conveniently located in or attached to the aforesaid flask assembly. FIGS. 2 and 3 illustrate two embodiments of the cell culture reactor with an attached settling chamber which are preferably employed in the method of the present invention.

Now with particular reference to FIG. 2, reference numeral 35 refers generally to the cell culture reactor or flask which is used for the agitated suspension culturing of mammalian and other animal cells on microcarriers. The flask preferably is made of clear glass or non-toxic rigid plastic materials but also can be made of biocompatible metals such as, for example, stainless steel. The flask is shown to have a generally cylindrical form with sidewalls 36, bottom 37, neck portion 38 and mouth 39. It will be appreciated, however, that other configurations of the flask or culture vessel can be employed.

In FIG. 2 the mouth of the flask is shown to be closed with a removable stopper 40 having a single hole in its center. It will be appreciated, of course, that the flask preferably will be provided with additional openings which are adapted for other gas and liquid inlet and outlet purposes such as, for example, inlet of oxygen, carbon dioxide, $NaHCO_3$ solution and the like. These openings can be placed in the stopper 40 itself or in separate openings in the flask walls.

Flask 35 is shown to be partially filled with culture fluid 41 in which the microcarriers 42 and attached cells 43 are suspended (both enlarged in size and proportions for illustrative purposes).

Positioned vertically in the flask is a rotatable agitator unit 45 which is suspended downwardly from the top by a stationary shaft 46. Shaft 46 is adapted to frictionally fit in the central opening or hole of stopper 40.

The agitator unit 45 is shown to have a rotatable sleeve member 47 journaled for rotation about the stationary shaft 46, a cross piece member 48 fixed in said sleeve member and having a longitudinal axis transverse to the vertical axis of said shaft, a pair of arms 49 downwardly depending from opposite ends of said cross piece member, and a relatively thin, flexible sheet 50 suspended between said arms. The flexible sheet is fastened to the agitator arms, such as by wire means, only at the lower end of each arm and at an upper position, such as, e.g., at about a mid-point 51, along the length of each arm and left unfastened between these attachment points on each arm. A magnetic stirrer bar 52 is also shown to be removably fastened to the lower ends of the agitator arms. The agitator unit can be caused to rotate about shaft 46 by activation of a revolving U-shaped or bar magnet (not shown) positioned under the cell culture flask. An arrow indicates the direction of the rotation.

Sheet 50 preferably has flexibility such as to allow it to yield to the influence of the liquid flow during rotation of the agitator whereby it can billow out like a sail and assume a concave forward facing configuration. The flexible sheet also remains unattached to the agitator arms for a substantial distance intermediate the upper and lower attachment points to permit such billowing.

The relatively thin, flexible agitator sheet 50 can be made of fine mesh cloth or fabric, plastic film or metal foil, and other such permeable or impermeable flexible sheet materials, for example, a nylon screen cloth or a flexible fiberglass sheet. A mono screen nylon cloth available under the trademark NITEX ® from Tetko, Inc., of Elmsford, N.Y., having nominal mesh openings of about 110$\mu$ and a thickness of about 0.005 inch (0.0127 cm) is eminently suitable for use in this invention.

During rotation, the agitator unit of FIG. 2 has the appearance of a bowed swing with the stirrer bar representing the swing's seat. The flexible sheet 50 is shown to have an inverted trapezoidal shape in which the upper side of the sheet is preferably longer than the lower side of the sheet to provide additional freedom for the sheet to flex and billow like a sail with the liquid flow during rotation of the agitator unit. The arms of the agitator can be made of a relatively flexible material such as silicone tubing to further facilitate the billowing effect of sheet 50 during such rotation. During operation of the agitator the level of the culture fluid in the culture flask preferably is kept above the flexible sheet but below the bearing means in the sleeve member.

Other configurations of the agitator unit as described in the aforesaid copending application Ser. No. 161,614, filed June 20, 1980, can also be used in the method of the present invention.

In FIG. 2, the settling chamber is indicated generally by reference numeral 55. The settling chamber is shown to have a generally cylindrical sidewall 56 with an inverted conical bottom 57 that empties through a tubular portion 58 into sidearm 59 which, in turn, leads directly into the cell culture flask at a point below the surface of the culture medium. The settling chamber 55 is shown to be connected to arm 59 through a glass O-ring joint 60. At the top of the settling chamber, a tube 61 (shown in part) leads to a satellite filter flask as described hereinbefore. The settling chamber also is equipped with a multihole flow distributor 62 to prevent channeling through the chamber. The conical bottom has a tapering surface with a slope (shown by arcs 63) ranging from about 15° to about 60°, and preferably from about 30° (as illustrated) to about 45°, from vertical to facilitate the desired microcarrier bead-cell contact. Similar sloping surface in tube 58 and arm 59 further enhances such contact. The volume of the settling chamber preferably should be sufficient to allow complete settling of the carrier beads at the maximum flow rate used in the recycling system. The recycle system can be reversed periodically to ensure free flow of settling beads and can have on and off phases. Use of a double headed recycle pump (shown for convenience as individual pumps 26 and 28) which is controlled by polarity reversal and pulse timer system 31 is adapted to provide these alternative features.

FIG. 3 shows another embodiment of the settling chamber similar to that of FIG. 2 but positioned vertically on top of the cell culture reactor (shown in part) instead of angled inwardly from the side. The cell culture reactor 65 has a central top opening 66 and a sidearm opening 67 which is closed with a one-holed stopper 68. Settling chamber 69 has a lower funnel portion with inwardly tapering surface 70 and a tubular extension 71 leading directly into the cell culture reactor below the surface 75 of the liquid contents. The conical bottom 70 as illustrated has a slope of about 30° (shown by arcs 72) from vertical. The settling chamber also is equipped with a flow distributor 74 and an opening at the top to tube 73 (shown in part) which leads to a satellite filter vessel.

The satellite filter vessel can be similar to the flask apparatus shown in U.S. Pat. No. 4,184,916 having a rotating filter unit suspended downwardly from the top, or the flask apparatus shown in U.S. Pat. No. 4,178,209 in which a stationary filter unit suspended downwardly from the top has a rotatable agitator concentrically disposed about the filter unit. Preferably, the rotatable agitator has a flexible sheet configuration as described in the aforesaid copending application Ser. No. 161,614, filed June 20, 1980. The rotating agitator aids in the prevention of plugging of the filter which is caused by cell debris carried over into the satellite filter vessel.

The culturing of cells in accordance with the present invention enables the production of a cell density per unit of area of from about 3 to about 4 times as great as that obtained for the same cells in conventional roller bottles. While microcarriers often have been reported to be more efficient for cell growth on the basis of volume of medium, they nevertheless heretofore have been less efficient than conventional roller bottle systems on a surface area basis. The temporary residence of the cells and microcarriers outside the main cell culture reactor agitation zone and in the settling chamber as described herein allows the individual cells and microcarrier particles to touch one another for much longer time periods than the momentary or transient contacts made during agitation in the cell culture reactor. After the microcarrier particles become confluent with cells, the cell bridges and aggregates form during this prolonged conjunction without being subjected to the limiting environment such as occurs when the cells and microcarrier particles are allowed to settle to the bottom of the cell culture reactor by periodically stopping the agitation as described in the prior art.* In the settling chamber, medium continues to be drawn over the settling cells and microcarier particles to produce a slow and gentle tumbling motion as the medium is recycled through the satellite filter vessel. When, instead, the cells and microcarriers are allowed to settle in the main cell culture reactor for an extended period to cause aggregation, the cells and microcarrier particles become too compacted and the cells tend to die. Depletion of nutrients and oxygen, high concentrations of waste products, and pH extremes which occur when cells settle out in the cell culture reactor can cause cell death or cell damage.

*See Horng and McLimans, *Biotechnol. Bioeng.* 17, 713–732 (1975), for limiting effects of growth in stationary petri dish culture of cells on microcarriers.

The production of large cell-microcarrier aggregates with increased cell area-densities in accordance with the method of this invention has a further advantage in release of the attached cells from the microcarrier support. One of the major limitations in the scale-up of human diploid fibroblasts in microcarrier culture is the difficulty of releasing these cells from the carriers so that they can be used to inoculate larger culture vessels. Such difficulty tends to prevent more than a one-stage scale-up from conventional monolayer culture. It has been found unexpectedly that at the high cell densities achieved by the present invention cells are more easily released with trypsin than at lower cell densities with no visible damage.

The following examples will further illustrate the invention although it should be understood that the invention is not limited to these specific examples.

EXAMPLE 1

A sample of AG1523 human diploid foreskin fibroblast cell line was obtained from the Institute for Medical Research, Camden, N.J., at passage 3. The cells were grown to confluency at 37° C. and subcultured through passage 14 in 75 cm$^2$ T-flasks (Falcon Plastics) and 690 cm$^2$ roller bottles containing Dulbecco's modification of Eagle's minimum essential medium (MEM) supplemented with 4.5. gm/liter of glucose and 10% fetal bovine serum without addition of any antibiotics. The cells were then grown in agitated suspension culture on microcarriers using the cell culture system and apparatus illustrated by FIG. 1 and described hereinbefore. The reactor system was maintained at a net flow rate of about 500 ml per hour. The recycle pumps were maintained in the on phase for ninety seconds and in the off phase for thirty seconds of each two minuted period. During each minute of on time, forty seconds were in the forward direction (i.e., reactor to settling bottle to filter vessel) and twenty seconds were in the reverse direction.

For use in the microcarrier cell culture reactor having a capacity of 4 liters, a total of 35 grams of microcarrier beads were prepared as follows:

Polyacrylamide Bio-Carriers (Bio-Rad Laboratories, Richmond, Calif.) with a swollen surface area of 16.5 m$^2$ or the equivalent of 239 roller bottles (each having 690 cm$^2$ available surface) were sterilized by autoclaving in aqueous buffer solution at pH 5.0 consisting of 0.05 M NaCl and 0.05 M 2(N-Morpholino)ethane sulfonic acid (MES). During autoclaving, the depth of the settled beads was less than two inches (<5.18 cm metric) and the temperature was maintained at 124° C. for about 40 to 60 minutes. After cooling, the beads were aseptically washed twice with phosphate buffered saline (PBS) and once with the aforesaid serum-containing medium. The PBS was prepared by dissolving 80 grams NaCl, 2 grams KCl, 2 grams KH$_2$PO$_4$ and 21.6 grams Na$_2$HPO$_4$.7H$_2$O in 10 liters distilled water, followed by autoclaving.

The microcarrier beads and fresh medium were added to the 4 liter cell culture reactor vessel and cells from nine roller bottles of the AG1523 cell line at passage 14 were used for inoculation. The reactor was equipped with a centrally disposed, rotatable agitator shaft with four flexible sheets equidistantly spaced apart from each other circumferentially about the vertical axis of said shaft and attached to the shaft at upper and lower positions. The reactor agitation rate was maintained from about 30 to about 40 rpm and the satellite filter vessel agitator at about 80 to 100 rpm during the cell growth period. The reactor also was equipped with a settling chamber of the type illustrated in FIG. 2 but which was connected to the sloping reactor side arm through a one-holed stopper as in FIG. 3 rather than an O-ring joint as shown in FIG. 2. The settling chamber had a volume of 155 ml. The upper part of the chamber had a diameter of 5 cm while the lower tubular extension had a diameter of 1.6 cm. After 257 hours of growth with this system, the cell density by nuclei count was $8.26 \pm 0.25 \times 10^6$ cells/ml or $33 \times 10^9$ cells total. This cell density represents the equivalent of 1100 roller bottles assuming the value of $3 \times 10^7$ cells/roller bottle. Nuclei counts were made substantially in accordance with the procedure reported by Sanford et al., *J. Natl. Cancer Inst.* 11, 773–(1951).

As the volume of swollen beads was approximately one-fourth the total volume of the suspension, various concentrations had to be adjusted for the nuclei count. A four ml sample was withdrawn and centrifuged two minutes at 100 to 300×g to pack the beads. The supernatant was removed and 0.2 M citric acid was added to the beads to a total volume of 2 ml. This mixture was slowly agitated 1 to 3 hours at 37° C. Then 2 ml. of 0.2% crystal violet in 0.1 M citric acid was added and stained nuclei were counted in a hemocytometer.

During the aforesaid agitated suspension culture on microcarriers, the initial inoculum of one to two cells per bead increased to cover the beads and then progressive aggregation of the beads was observed. Although some beads did not initially attach cells, most of these were recruited into the bead-cell aggregates during growth in this system. At the time of harvest, almost all the beads were contained in large aggregates of 5 to 20 bead diameters across. The cells grew on and between the beads and formed the appearance of a cocoon of cells surrounding each aggregate. A total of 29.2 liters of medium was used to produce the $33 \times 10^9$ cells. As compared to conventional 690 cm$^2$ roller bottles containing 100 ml of medium per bottle, the yield on the basis of actual surface area was 4.6 fold greater for the system of this example and 3.8 fold less medium was required than in the roller bottle system.

A portion of the cell-bead aggregates was washed four times in PBS and lysed by two freeze-thaw cycles in distilled water. The cell extract was then concentrated by carboxymethyl Sephadex chromatography and the protein fractions were found to be positive for angiogenic factor activity by the CAM (chorioallantoic membrane) assay in 10 to 11 day-old chick embryos in accordance with procedure described by Auerbach et al, *Devel. Biol.* 41, 391–4 (1974); Folkman, *Cancer Res.*, 34, 2109-13 and 36, 110-114 (1976).

Another portion of the cells was released by trypsin treatment as follows: the cell-bead aggregates were washed three times with PBS containing 0.02% EDTA and then incubated for 15 minutes with an equal volume of trypsin-EDTA solution (0.5 gm/liter porcine trypsin, GIBCO cat. #610-5300-TRYPSIN(1:250) National Formulary, Vol. 14, 1975, and 0.2 gm/liter EDTA in Hanks balanced salt solution). All of the cells were readily released with good viability.

EXAMPLE 2

AG 1523 cells from eleven roller bottles at passage 16 were used to inoculate about 45 grams of polyacrylamide Bio-Carriers in the 4 liter microcarrier reactor system as described in Example 1. The actual bead surface area was 21.2 m$^2$ which corresponds to 307 roller bottles (each haaving 690 cm$^2$ available surface). After use of 27.6 liters of medium in the cell culture reactor system, the cell density was $7.78 \pm 1.37 \times 10^6$ cells/ml or $31.1 \times 10^9$ cells total, which was the equivalent of 1,037 roller bottles. By comparison to the conventional roller bottle system this example provided a 3.4 fold increase in cells per unit area of surface and a 3.8 fold decrease in medium requirement. The formation of cell-bead aggregates was observed as in Example 1. Separate portions of the above cultured cells were then used to produce interferon and plasminogen activator.

INTERFERON PRODUCTION

One portion of the above bead-cell aggregates was aged in 2% serum and used for interferon production as follows: After maximal growth in the microcarrier reactor, an aliquot of microcarrier aggregates containing high densities of AG 1523 cells was removed, washed twice with serum-free medium and resuspended in medium supplemental with 2% fetal bovine serum. This 2% serum medium was changed three times over a five day aging period to maintain pH between about 6.8 and 7.2. A suspension vessel containing a single sheet flexible agitator as illustrated in FIG. 1 was used at about 40 rpm. A portion of these cells in microcarrier aggregates was washed twice with serum-free medium containing 50 µg/ml cycloheximide and then resuspended in serum-free medium containing 50 µg/ml cycloheximide and 100 µg/ml polyriboinosinic acid-polyribocytidylic acid (polyr I-polyr C). After gentle stirring for 4 hours at 37° C., Actinomycin C was added to a concentration of one µg/ml. After two more hours at 37° C., the carrier aggregates were washed four times with medium supplemented only with 2% fetal bovine serum and further incubated in this medium for 18-20 hours. This medium was then harvested, clarified by centrifugation and frozen. The samples were assayed for interferon by a standard procedure in which HeLa cells were challenged with poliovirus using Armstrong's modification of Finter's dye uptake method. See Finter, *J. Gen. Virol.* 5, 419-427 (1969) and Armstrong, *Appl. Microbiol.* 21, 723-726 (1971). Interferon titer of one international unit per 500 cells was obtained.

PLASMINOGEN ACTIVATOR PRODUCTION

Another portion of the above bead-cell aggregates was aged in 2% fetal bovine serum as above over a four day period. After the aging, the cell-microcarrier aggregates were washed several times in serum-free medium and resuspended in medium containing 5 mg/ml lactalbumin hydrolysate. The cells were gently agitated for seven days with one change of the lactalbumin hydrolysate medium. This medium was harvested, clarified by centrifugation and assayed for plasminogen activator activity by the fibrin dish assay procedure described by Feder et al., *Biochem. Biophys. Res. Comm.* 83, 1164–1170 (1978). One unit of plasminogen activator activity was defined as the amount of enzyme which solubilized one microgram of fibrin per hour. According to this procedure, a frozen aliquot of the lactalbumin hydrolysate medium was determined to have 1700 units/ml.

EXAMPLE 3

AG 1523 cells from 22 roller bottles at passages 13 and 14 were used to inoculate about 50 grams of polyacrylamide Bio-Carriers in the 4 liter microcarrier reactor system as described in Example 1. An agitation rate of about 18 rpm was used for the main cell culture reactor and about 80 rpm for the satellite filter vessel. The actual bead surface area was 23.5 m$^2$ which corresponds to 340 roller bottles (690 cm$^2$/bottle). A total of 27.6 liters of medium was used to produce a final cell density of $1.01 \pm 0.04 \times 10^7$ cells/ml or $4.04 \times 10^{10}$ cells total, which was the equivalent of 1347 roller bottles. By comparison to the conventional roller bottle system this example provided a 4 fold enhancement in cells per unit area of surface and a 4.9 fold decrease in medium requirement. The formation of cell-bead aggregates was observed as in Example 1. A portion of the cells were used for the production of angiogenesis factor while the remainder of the cells were released from the beads according to the following procedure: About one liter of settled aggregates was washed 3 times with 2 liters of a warm solution of PBS containing 0.02% EDTA each time. One hundred ml of 10×trypsin-EDTA solution (5 g/liter porcine trypsin and 2 g/liter EDTA in Hanks' balanced salt solution) then was added to the reactor. After agitation at about 100 rpm for 10 minutes at 37° C., all of the cells were released from the beads and then used to inoculate the 44 liter reactor of Example 4. Ninety-two percent of the cells were viable and attached to the new carriers.

ANGIOGENSIS FACTOR PRODUCTION

A small aliquot of the above cell-microcarrier aggregates was washed three times with PBS, resuspended in 4 M KCl, and incubated at room temperature (ca-20–25° C.) with periodic mixing for 90 minutes. After dialysis, the supernatant was lyophilized and assayed for angiogenic factor activity by the CAM assay. The nonsolubilized material was further processed by freezethaw in 4 M KCl and the supernatant dialyzed, lyophilized and assayed. The CAM assay results of samples at three different concentrations are as follows:

| KCl Treatment Only: | |
|---|---|
| µg protein | activity |
| 200 | 5 of 10 eggs positive |
| 60 | 4 of 10 eggs positive |
| 20 | 4 of 10 eggs positive |
| KCl + Freeze-thaw: | |
| µg protein | activity |
| 200 | 9 of 10 eggs positive |
| 60 | 6 of 10 eggs positive |
| 20 | 5 of 10 eggs positive |
| Control Samples: | |

| | |
|---|---|
| Negative Control (200 μg) | 0 of 10 eggs positive |
| Positive control (50 μg) | 6 of 10 eggs positive |

EXAMPLE 4

AG 1523 cells produced as described in Example 3 were used to inoculate 400 grams of autoclaved polyacrylamide Bio-Carriers including the remaining beads (ca. 50 gms.) and remaining cells from the 4 liter reactor of Example 3. These cells were grown in a reactor system as described in Example 1 except that a 44 liter reactor was used which was equipped with a settling chamber of the type shown in FIG. 3. The settling chamber had a volume of 1040 ml. The upper part of the chamber had a diameter of 11 cm while the lower tubular extension had a diameter of 1.8 cm. The reactor system was maintained at a flow rate of about 4 liters per hour with no reverse flow. The micro-carrier beads were prepared as in Example 1 except that after autoclaving they were washed three times with serum-free medium. Serum-free medium and fetal bovine serum were then added to about 10 liters of swollen beads to a final value, after inoculation, of 44 liters at 10% serum. An agitator rate of 8 to 12 rpm was used for the reactor and 80 rpm for the satellite filter vessel. The actual bead surface area was 188 m$^2$ which is equivalent to 2725 roller bottles (690 cm$^2$/bottle). A total of 262.7 liters of medium was used to produce a cell density of $7.68 \pm 0.55 \times 10^6$ cells/ml or $3.38 \times 10^{11}$ cells total, which was the equivalent of 11,264 roller bottles. In comparison with the conventional roller bottle system, this example provided a 4.1 fold enhancement in cells per unit area of surface and a 4.2 fold decrease in medium requirement. The formation of cell-bead aggregates was observed as in Example 1.

PLASMINOGEN ACTIVATOR PRODUCTION

A portion of the cell-bead aggregates was washed four times with serum-free medium and returned to the reactor vessel with 44 liters of medium containing 5 mg/ml lactalbumin hydrolysate. The pH was controlled to a level of about 7.0 to 7.1 by adjustment of the $CO_2$-air mixture in the overlay gases and by addition of $NaHCO_3$ solution. After 5 days the supernatant was harvested and the reactor filled with fresh lactalbumin hydrolysate medium. After an additional six days the supernatant was again harvested. Both supernatants were concentrated about 10–15 fold in commercial hollow fiber and membrane concentrators. A portion of each concentrated supernatant was dialyzed and lyophilized and another portion of each concentrated supernatant was frozen. Both lyophilized and frozen samples were assayed for plasminogen activator activity as in Example 2. High levels of activity were determined in both the lyophilized and frozen material as follows:

| | 1st Harvest | 2d Harvest |
|---|---|---|
| Lyophilized | 22,000 units/ml | 18,500 units/ml |
| Frozen | 10,000 units/ml | 10,500 units/ml |

EXAMPLE 5

AG 1523 cells from 25 roller bottles at passage 19 were used to inoculate 50 grams of autoclaved polyacrylamide Bio-Carriers in the 4 liter microcarrier reactor system as described in Example 1 with a settling chamber of the type illustrated in FIG. 2. The settling chamber had a volume of 200 ml. The upper part of the chamber had a diameter of 5 cm and the lower tubular extension had a diameter of 3.3. cm. The reactor system was maintained at a flow rate of about 500 ml per hour with no reverse flow. In this example, the medium was supplemented in several passages (15 to 19 ) with 6% bovine calf serum instead of the 10% fetal bovine serum used in Example 1. The 6% bovine calf serum supplement also was used in the 4 liter reactor. The agitation rate in the reactor was 16 rpm and in the satellite filter vessel was 80 rpm. The actual bead surface area was 23.5 m$^2$ which corresponds to 340 roller bottles (690 cm$^2$/bottles). A total of 31 liters of medium was used to produce a final cell density of $1.04 \pm 0.08 \times 10^7$ cells/ml or $4.16 \times 10^{10}$ cells total. In comparison to the conventional roller bottle system, this Example provided a 4 fold enhancement in cells per unit area of surface and 4.5 fold decrease in medium requirement. The formation of cell-bead aggregates was observed as in Example 1.

INTERFERON PRODUCTION

After completion of the growth period, the cell-bead aggregates were washed two times with serum-free medium resuspended in medium supplemented with 2% bovine calf serum and reconnected to the microcarrier reactor system with 2% bovine calf serum used with medium in the reactor vessel and satellite filter vessel. Ten liters of the 2% bovine calf serum supplemented medium were perfused through the reactor system over a nine-day period. Portions of the cell-bead aggregates were removed at various times and interferon was induced and assayed as described in Example 2. Levels of interferon increased to a maximum of 500 cells/international unit at 3 days as follows:

| Aging Time | Cells/unit |
|---|---|
| 0 days | 2000 |
| 3 days | 500 |
| 6 days | 4000 |
| 9 days | 6000 |

While in the foregoing examples particular cell culture media and microcarriers were used, it will be appreciated that the method of the invention is not limited to these particular media and microcarriers. Thus, the invention is adaptable to use with any of the well known tissue culture media such as, for example, Basal Medium Eagle's (BME), Eagle's Minimum Essential Medium (MEM), Dulbecco's Modified Eagle Medium, Medium 199 and the like. These are commercially available tissue culture media and are described in detail by H. J. Morton, In Vitro, 6, 89–108 (1970). These conventional culture media contain known essential amino acids, mineral salts, vitamins and carbohydrates. They are also frequently fortified with mammalian sera such as fetal bovine serum.

The microcarriers can be formed of inorganic materials such as glass beads, silica spherules, and the like or can be prepared as microspheres of organic polymeric materials such as DEAE-Sephadex, polyacrylamide, polyacrylonitrile, polystyrene latex particles and similar such microcarrier materials. Commercially available microcarriers especially adapted for cell culture are the polyacrylamide Bio-Carriers described hereinbefore, the Cytodex 1 microcarriers available from Pharmacia Fine Chemicals, Piscataway, New Jersey, and the Superbead microcarriers available from Flow Laboratories, Inc., McLean, Virginia.

Although the invention is especially useful with human diploid cells the invention is adaptable to all types of animal cells including, for example, mammalian, fowl and amphibian cells. Primary cells taken from embryonic, adult or tumor tissues as well as of established cell lines can thus be used. Examples of typical such cells are primary rhesus monkey kidney cells, baby hamster kidney cells, pig kidney cells, mouse embryo fibroblasts, normal human lung embryo fibroblasts, HeLa cells, primary and secondary chick fibroblasts, and various cells transformed with SV-40 or polyome virus.

After suitable growth of the cells, the cells can be harvested and further treated for the production of desired products by various means. For example, human diploid foreskin fibroblasts cultured by the method of this invention can be treated for the production of angiogenic factor, plasminogen activator and interferon. Angiogenic factor can be isolated from the growth medium or from the cells. Plastiminogen activator can be harvested from a serum-free maintenance medium during a period of aging after the cells have reached their maximum density. Interferon can be induced in the aged fibroblasts and its production enhanced due to the high cell density in the cell-microcarrier aggregates.

Various other examples and modifications of the foregoing examples will be apparent to the person skilled in the art after reading the present disclosure without departing from the spirit and scope of the invention and it is intended that all such examples and modifications be included within the scope of the appended claims.

What is claimed is:

1. In a method of growing anchorage-dependent cells in agitated microcarrier suspension culture, the improvement comprising aggregating the microcarriers and cells by periodically providing a temporary residence of said microcarriers and cells outside the main cell culture reactor agitation zone and in a separate compartment wherein they are subjected to a gentle tumbling action within a confined space having substantially the same environmental conditions as in said main cell culture reactor agitation zone and thereafter recycling said microcarriers and cells to said main cell culture reactor agitation zone.

2. The method of claim 1 in which the microcarriers and cells are periodically carried into and allowed to settle in a tumbling zone of confined space by perfusion of the suspension culture medium through said zone and into a satellite vessel under the force of a pressure differential.

3. The method of claim 2 in which the cell culture medium is recycled from the satellite vessel to the main cell culture reactor.

4. The method of claim 1 in which the microcarriers and cells are periodically carried into and allowed to settle in a settling chamber having an inverted conical configuration with a narrow opening at the vertex which empties into the main cell culture reactor.

5. The method of claim 4 in which the microcarriers and cells are periodically carried into and allowed to settle in the settling chamber by the perfusion of the suspension culture medium through said settling chamber and into a satellite vessel under the force of a pressure differential.

6. The method of claim 5 in which the cell culture medium is recycled from the satellite vessel to the main cell culture reactor.

7. The method of claim 1 in which the cells are human diploid foreskin fibroblast cells.

8. The method of claim 7 in which the cells are treated for the production of interferon.

9. The method of claim 7 in which the cells are treated for the production of plasminogen activator.

10. The method of claim 7 in which the cells are treated for the production of angiogenic factor.

* * * * *